(12) United States Patent
Hagfors et al.

(10) Patent No.: US 12,396,684 B2
(45) Date of Patent: Aug. 26, 2025

(54) SYSTEM AND METHOD FOR VISUALIZING A PROXIMITY OF A CATHETER ELECTRODE TO A 3D GEOMETRY OF BIOLOGICAL TISSUE

(71) Applicant: St. Jude Medical, Cardiology Division, Inc., St. Paul, MN (US)

(72) Inventors: Mark Hagfors, North Oaks, MN (US); Michael Quinn, St. Paul, MN (US); Wenwen Li, San Jose, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1388 days.

(21) Appl. No.: 16/640,394

(22) PCT Filed: Aug. 28, 2018

(86) PCT No.: PCT/US2018/048268
§ 371 (c)(1),
(2) Date: Feb. 20, 2020

(87) PCT Pub. No.: WO2019/046250
PCT Pub. Date: Mar. 7, 2019

(65) Prior Publication Data
US 2020/0359968 A1    Nov. 19, 2020

Related U.S. Application Data
(60) Provisional application No. 62/553,189, filed on Sep. 1, 2017.

(51) Int. Cl.
*A61B 5/00*    (2006.01)
*A61B 5/0538*    (2021.01)
(Continued)

(52) U.S. Cl.
CPC .......... *A61B 5/6886* (2013.01); *A61B 5/0538* (2013.01); *A61B 5/066* (2013.01);
(Continued)

(58) Field of Classification Search
CPC ............................. A61B 5/6886; G16H 30/40
See application file for complete search history.

(56) References Cited

U.S. PATENT DOCUMENTS

2010/0268059 A1* 10/2010 Ryu ...................... A61N 1/3627
600/407
2011/0160569 A1*  6/2011 Cohen .................... A61B 5/064
600/424
(Continued)

FOREIGN PATENT DOCUMENTS

WO    WO-2006060613 A1 *  6/2006   ............... A61B 6/12

OTHER PUBLICATIONS

International Search Report and Written Opinion for International Application No. PCT/US2018/048268, mailed Nov. 30, 2018, 8 pages.

*Primary Examiner* — Benjamin J Klein
*Assistant Examiner* — Thien Jason Tran
(74) *Attorney, Agent, or Firm* — Billion & Armitage (57) ABSTRACT

The present disclosure provides an electrophysiology system to facilitate visualizing a proximity of at least one catheter electrode to a 3D geometry of a biological tissue. The system includes a computing device including at least one processor in communication with a memory, wherein the processor is configured to determine the proximity between the at least one catheter electrode and the biological tissue using at least one measurement. The system further includes a display device configured to display the 3D geometry of the biological tissue and a visual effect illus-
(Continued)

trating the proximity between the at least one catheter electrode and the biological tissue.

20 Claims, 6 Drawing Sheets

(51) Int. Cl.
*A61B 5/06* (2006.01)
*G16H 30/40* (2018.01)

(52) U.S. Cl.
CPC .......... *A61B 5/6852* (2013.01); *A61B 5/6869* (2013.01); *A61B 5/742* (2013.01); *G16H 30/40* (2018.01); *A61B 5/068* (2013.01)

(56) References Cited

U.S. PATENT DOCUMENTS

2017/0365051 A1* 12/2017 Wahrenberg ........... A61B 90/37
2018/0360342 A1* 12/2018 Fuimaono .......... A61N 1/36117

* cited by examiner

SYSTEM AND METHOD FOR VISUALIZING A PROXIMITY OF A CATHETER ELECTRODE TO A 3D GEOMETRY OF BIOLOGICAL TISSUE

CROSS REFERENCE TO RELATED APPLICATIONS

This application is the national stage entry of PCT/US2018/048268, filed Aug. 28, 2018, which claims priority to U.S. provisional application Ser. No. 62/553,189, filed Sep. 1, 2017, which are incorporated herein by reference in their entirety.

A. Field of the Disclosure

The present disclosure relates generally to medical systems that are used in the human body. In particular, in many embodiments, the present disclosure relates to 3D electrophysiology navigation and mapping systems allowing for visualization of the proximity from at least one electrode to cardiac geometry.

B. Background

Electrophysiology studies provide testing that helps physicians understand the nature of the heart muscle by testing the electrical activity of the heart. For example, abnormal heart rhythms can be detected during said testing. The results help determine if an individual needs to correct an abnormal heart rhythm by medical means, including but not limited to, medicine, a pacemaker, an implantable cardioverter defibrillator, cardiac ablation, and/or surgery. Cardiac arrhythmias, for example are sometimes treated using ablation therapy. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter) . Physicians are able to advance said catheters through the individual's blood vessels and into the heart. Electrical signals produced by the heart may be detected by the catheters and recorded using cardiac mapping, allowing the physician to locate the abnormality within the heart. This allows the physician to view, on a screen, a digital geometric model of the heart along with the location of the catheter while the catheter is being guided through the heart.

Procedures such as electrical mapping and catheter ablation require an accurate visual model to perform the most efficient procedure. To provide the most accurate results, the proximity between one or more electrodes and the cardiac tissue needs to be illustrated in a straightforward and intuitive manner.

BRIEF SUMMARY OF THE DISCLOSURE

The present disclosure generally relates to electrophysiology navigation and mapping systems.

In one embodiment, the present disclosure is directed to an electrophysiology system to facilitate visualizing a proximity of at least one catheter electrode to a 3D geometry of a biological tissue. The system includes a computing device including at least one processor in communication with a memory, wherein the processor is configured to determine the proximity between the at least one catheter electrode and the biological tissue using at least one measurement. The system further includes a display device configured to display the 3D geometry of the biological tissue and a visual effect illustrating the proximity between the at least one catheter electrode and the biological tissue.

In another embodiment, the present disclosure is directed to a method for displaying a distance between at least one electrode and a 3D geometry of a biological tissue during 3D electrophysiology. The method includes determining a proximity between the at least one electrode and the biological tissue using at least one measurement using a computer including at least one processor in communication with a memory. The method further includes displaying, on a display device, a 3D geometry of the biological tissue and a visual effect that indicates the proximity between the at least one electrode and the biological tissue.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical systems devices that are used in the human body. In particular, in many embodiments, the present disclosure relates to an electrophysiological system for mapping electrodes during catheter navigation. The disclosed embodiments may lead to more consistent and improved patient outcomes with therapy, diagnostic, navigation, and/or mapping performed using a catheter. It is contemplated, however, that the described features and methods of the present disclosure as described herein may be incorporated into any number of systems as would be appreciated by one of ordinary skill in the art based on the disclosure herein.

The disclosure provides a system that enables visualizing the proximity between at least one catheter electrode and a 3D geometry of a biological tissue for mapping. In the example embodiment, biological tissue includes cardiac tissue from a human and/or animal heart. The 3D geometry is a digital reconstruction of the biological tissue. The 3D geometry or geometries can be constructed or imported using other known imaging modalities, including but not limited to, computed tomography and/or magnetic resonance imaging. The system is used for mapping during 3D electrophysiology navigation, wherein catheters including electrodes are placed in cardiac chambers. Using the system determined herein, the catheter(s) can be located and tracked in real time. The tracking accuracy of the system allows for a non-invasive medical procedure to monitor the rhythm of a heart muscle. The catheter may be any catheter suitable for electrically mapping a biological tissue, such as cardiac tissue.

In the example embodiment, during an electrophysiological procedure, a physician guides a catheter including multiple electrodes into a blood vessel and eventually into the heart. The catheter is configured to communicate, wirelessly or wired, with a computing device configured to determine the proximity between the multiple electrodes and the cardiac tissue using at least one measurement. The computing device includes at least one processor in communication with a memory.

In the example embodiment, the at least one measurement includes the shortest distance from the location of the at least one electrode to the geometry surface of the biological tissue. Another measurement includes contact force. The contact force is a positive value when the at least one electrode is in contact with the biological tissue surface. The contact force is a measured force (i.e., grams) exerted by the catheter's distal electrode upon the endocardial tissue. A force sensing catheter typically uses pressure transducers to determine the magnitude and direction of the force on the tissue at the catheter tip. Another measurement includes an electrode-tissue coupling index value. The coupling index is a measurement of the degree of coupling between an electrode and the endocardial tissue. This measurement is derived from the first and second components of a complex impedance (e.g., resistance and reactance or impedance magnitude and phase angle). Additional details of the electrode-coupling index may be found in U.S. Patent Application Publication 2009/0275827 and U.S. Pat. Nos. 8,449,535 and 8,406,866, each of which is incorporated herein by reference in its entirety. Another measurement includes a Peak to Peak voltage value of an electrogram at the at least one electrode. The peak to peak voltage measurement increases when good contact between the tissue and the electrode is established. In other embodiments the at least one measurement may include any other measurement suitable for indicating the proximity between a catheter electrode and a biological tissue. Additional suitable measurements and/or additional details on the measurements described herein may be found in U.S. Patent Application Publications 2009/0163904 and 2017/0007323, each of which is incorporated herein by reference in its entirety.

The computing device is further configured to communicate with a display device. The display device provides the physician with a real-time view of the catheter inside the biological tissue, allowing for accurate catheter navigation. The display device includes any type of device suitable for displaying digital projections, such as a 3D geometric model of a biological tissue and/or model.

To properly display the location of the catheter relative to the biological tissue, the measurements are combined and translated into a 3D reconstructed catheter and placed alongside the reconstructed 3D geometry of the biological tissue. The computing device displays a visual effect, based upon the at least one measurement, showing the proximity between the electrodes within the catheter and the biological tissue. In the example embodiment, the visual effect is a digital 2D effect, oftentimes having a substantially circular shape, that highlights various degrees of proximity. This effect shall herein be referred to as a "spotlight" effect. The spotlight effect, or spotlight, appears on the reconstructed 3D geometry of the digital display corresponding to the catheter's position to the actual biological tissue. For example, as the physician moves the catheter closer to a location on the biological tissue, the spotlight becomes brighter on the corresponding reconstructed 3D geometry.

The visual effect includes attributes that correspond to the actual proximity between the catheter electrodes and the biological tissue. This further provides accurate electrical mapping of the catheter and the biological tissue. In the example embodiment, as explained above, one attribute includes a change in brightness of the visual effect as the proximity of the electrode and the biological tissue changes. For example, as the proximity between the electrode and the biological tissue decreases (i.e., as the electrode moves closer to the biological tissue), the brightness of the spotlight increases on the corresponding position of the reconstructed 3D model of the biological tissue.

Another attribute includes a change in color intensity of the visual effect. For example, as the proximity between the electrode and the biological tissue decreases, the intensity of the color on the reconstructed 3D geometry near the spotlight increases. Yet another attribute includes a decrease of the diffuseness of the visual effect. For example, as the proximity between the electrode and the biological tissue decreases, the diffuseness of the visual effect decreases, showing a smaller and more focused visual effect on the reconstructed 3D geometry. Yet another attribute includes a change in transparency of the reconstructed 3D geometry surface relative to the proximity between the electrode(s) and the reconstructed 3D geometry. For example, locations of the displayed reconstructed 3D geometry may become less transparent as the proximity between the electrode(s) and the biological tissue decreases (i.e., as the electrode moves closer to the biological tissue). Alternatively, locations of the displayed reconstructed 3D geometry may become more transparent as the electrode moves closer to the biological tissue. Further, in some embodiments, the locations may be opaque, without any change in transparency as the electrode moves closer to the biological tissue.

Figure 1:
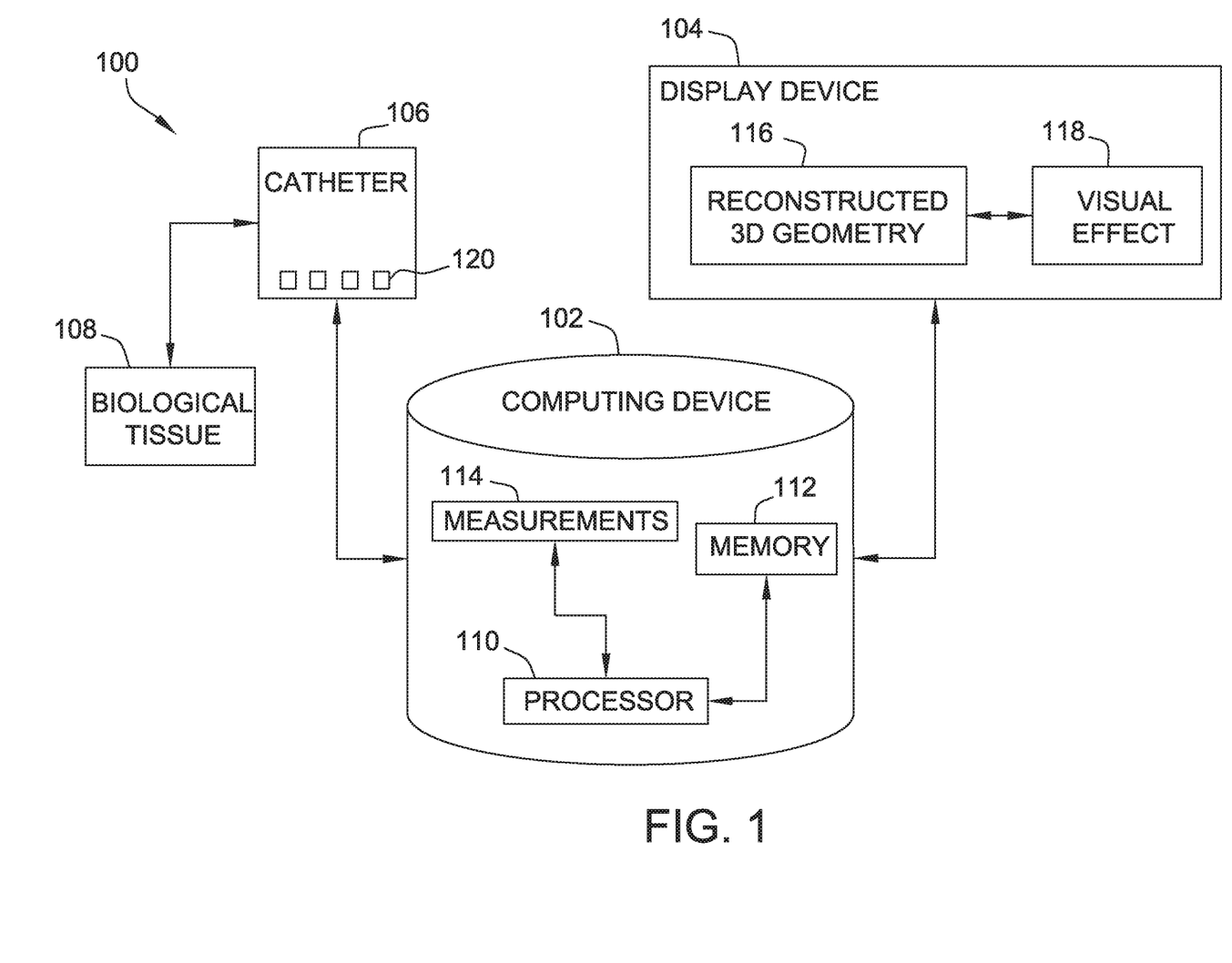
FIG. 1 is a schematic and block diagram view of an electrophysiological system for mapping electrodes during catheter navigation.

Referring now to the drawings, FIG. 1 is a schematic and block diagram view of an electrophysiological system 100 for mapping electrodes during catheter navigation. System 100 includes a computing device 102 configured to communicate with at least one of a display device 104 and/or a catheter 106. Computing device 102 includes at least one processor 110 in communication with at least one memory 112. Display device 104 is configured to display a digital image. Specifically, display device 104 is configured to display a reconstructed 3D geometry 116 along with a visual effect 118. Reconstructed 3D geometry 116 is herein described as geometry 116.

As described above, display device 104 includes any display device suitable for displaying geometry 116 or geometries 116 that are constructed or imported using other known imaging modalities, including but not limited to, computed tomography (CT), intracardiac ultrasound echocardiography (ICE), and/or magnetic resonance imaging (MRI). In some embodiments, display device 104 and computing device 102 are the same device. Geometry 116 is an image of a digital reconstruction of the biological tissue 108 used for navigating a catheter 106 within the biological tissue. In the example embodiment, biological tissue 108 is cardiac tissue, and geometry 116 is a digital reconstruction of a human or animal heart muscle. Catheter 106 includes at least one electrode 120 for electrical mapping of biological tissue 108. In the example embodiment, catheter 106 is an electrophysiology catheter suitable for electrically mapping a human heart for providing real-time images in vivo of biological tissue regions. In some embodiments, catheter 106 is an ablation catheter capable of both mapping and therapy.

In the example embodiment, catheter 106 may be coupled to a tracking device (not shown) and electrode(s) 120 to generate location signals associated with biological tissue 108. Processor 110 registers the detected electrical activity using the location signals from the tracking device and electrode(s) 120. Processor 110 then transmits an output signal with the electrical activity signals to display device 104.

In some embodiments, system 100 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories. The localization and mapping systems described in the following patents (all of which are hereby incorporated by reference in their entireties) can also be used: U.S. Pat. Nos. 6,990,370; 6,978,168; 6,947,785; 6,939,309; 6,728,562; 6,640,119; 5,983,126; and 5,697,377.

Processor 110 is further configured to determine the proximity between at least one electrode 120 and biological tissue 108 using at least one measurement 114. In the example embodiment, measurement 114 includes the shortest distance from the location of at least one electrode 120 to the surface of biological tissue 108. Another measurement 114 includes a contact force. The contact force is a positive value when at least one electrode 120 is in contact with a surface of biological tissue 108. Another measurement 114 includes an electrode-tissue coupling index value. The electrode-tissue coupling index value is determined from the complex impedance measured when a voltage is applied to at least one electrode 120. Yet another measurement 114 includes a Peak to Peak voltage value of an electrogram of at least one electrode 120. In other embodiments, the at least one measurement may include any other measurement suitable for indicating the proximity between a catheter electrode and a biological tissue.

As described above, visual effect 118 is a digital display effect used to indicate the location of catheter 106, specifically electrode(s) 120, relative to biological tissue 108. At least one measurement 114 is used to determine a proximity between electrode 120 and biological tissue 108, and the determined proximity is translated into a 3D image of catheter 106. Visual effect 118 is placed alongside geometry 116 of the biological tissue to indicate to a user, or a physician, the location of catheter 106 in relation to biological tissue 108.

Display device 104 displays visual effect 118 alongside geometry 116, based upon at least one measurement 114, showing the proximity between electrodes 120 within catheter 106 and biological tissue 118. This provides a real-time map of catheter 106 and biological tissue 108. In the example embodiment, visual effect 118 is a digital 2D circle effect that highlights various degrees of proximity between electrode(s) 120 and biological tissue 108. Additionally or alternatively, visual effect 118 may be any other visual effect that highlights various degrees of proximity between electrode(s) 120 and biological tissue 108

Figure 2:
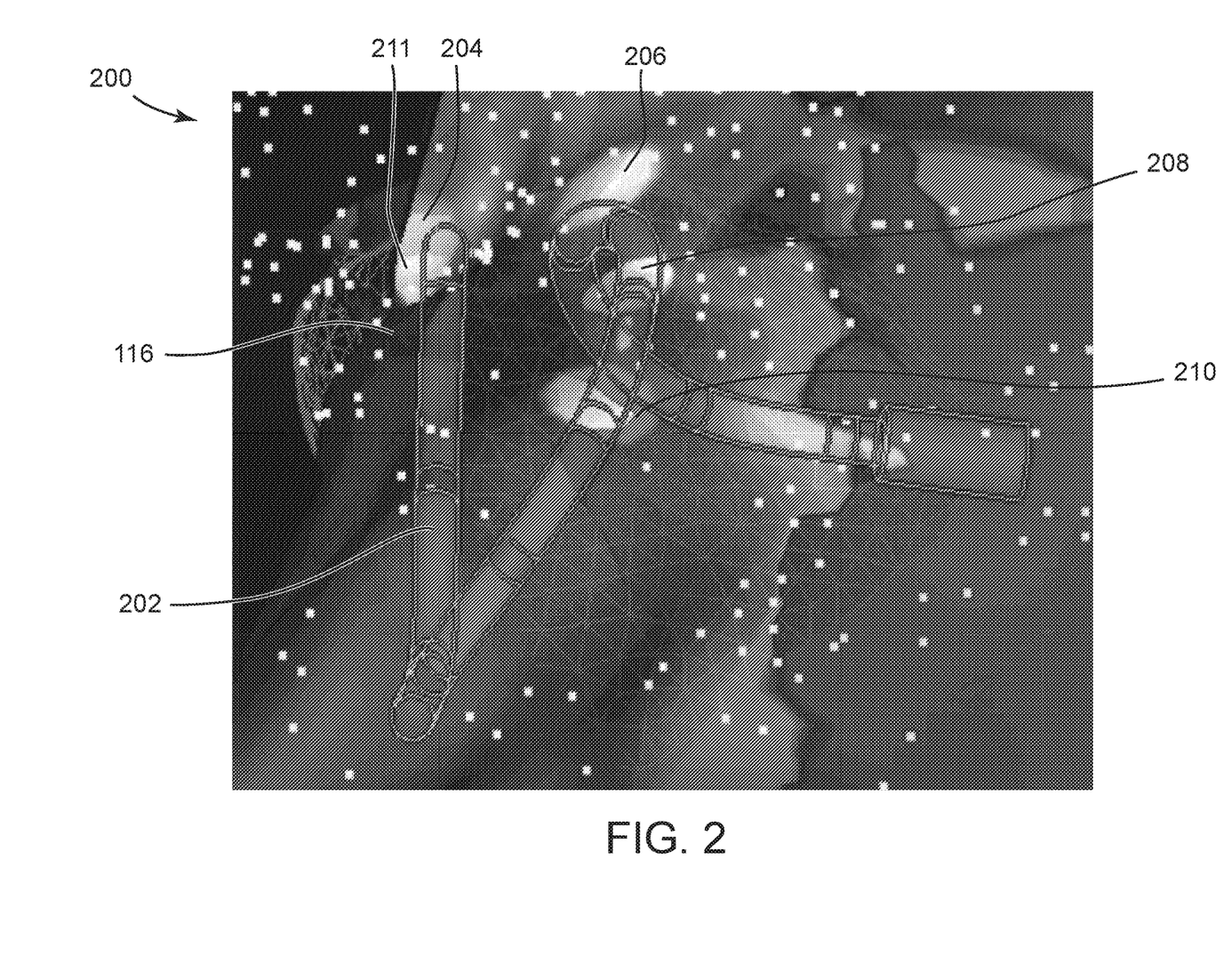
FIG. 2 is an electrophysiological map showing a catheter at a first location inside cardiac tissue displaying a visual effect that facilitates determining the location of multiple electrodes.
Figure 3:
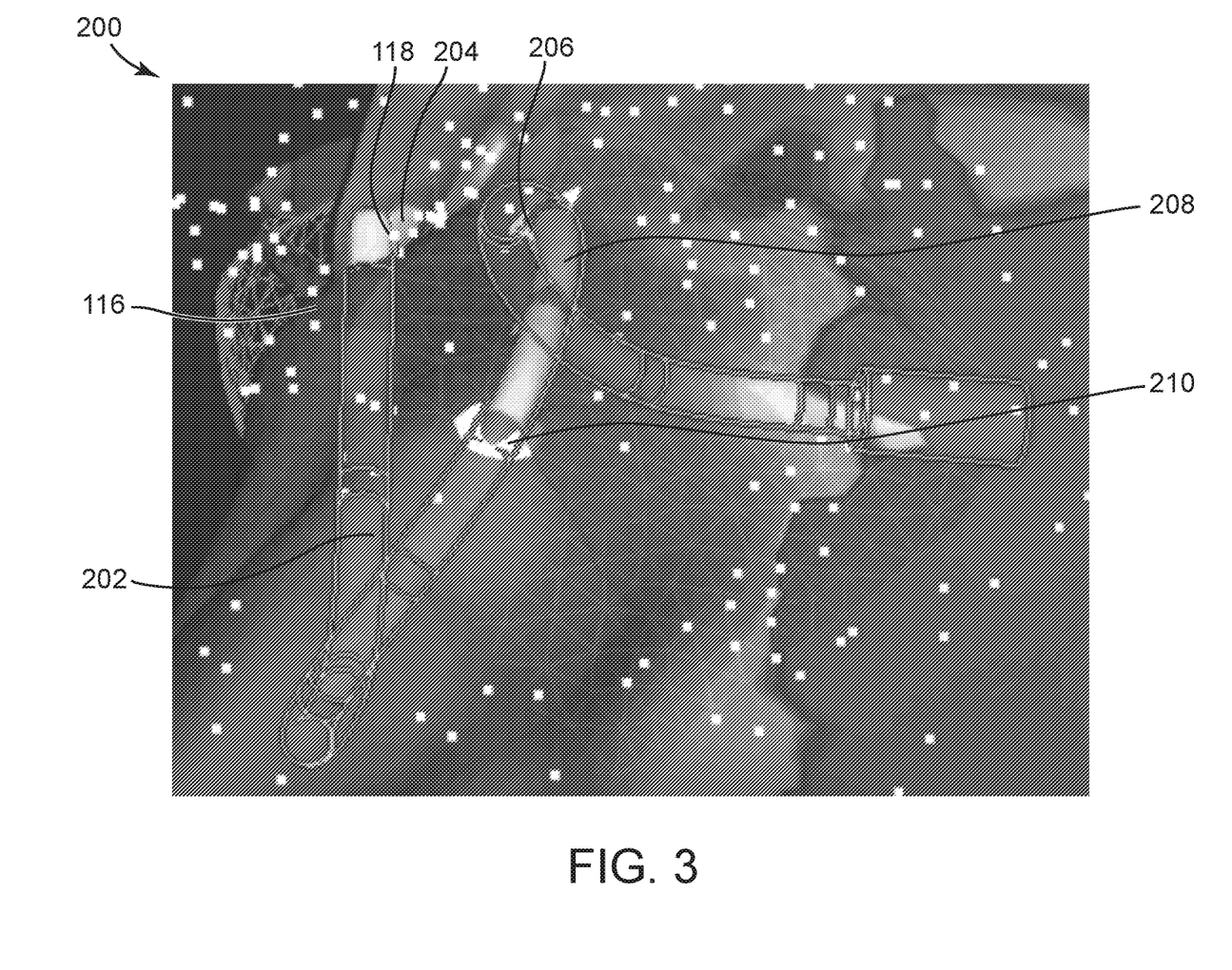
FIG. 3 is an electrophysiological map showing a catheter at a second location inside cardiac tissue displaying a visual effect that facilitates determining the location of multiple electrodes.

FIG. 2 and FIG. 3 are electrophysiology maps 200 and 300 of system 100. Electrophysiology maps 200 and 300 illustrate geometry 116 alongside visual effect 118 and a catheter image 202. Catheter image 202 is a digitally reconstructed image representing catheter 106 in relation to biological tissue 108. Maps 200 and 300 illustrate several exemplary variations in attributes of visual effects 118 relative to the proximity between electrode(s) 120 and biological tissue 108. Display device 104 is configured to display maps 200 and 300.

As described above, in the example embodiment, visual effect 118 is a digital 2D circle effect that highlights various degrees of proximity between electrode(s) 120 and biological tissue 108. This is what is referred to as the "spotlight" effect. The spotlight effect, or spotlight, appears on reconstructed 3D geometry 116 of digital display device 104 corresponding to catheter's 106 position relative to biological tissue 108. For example, as the physician moves catheter 106 from a first position (FIG. 2) to a second position (FIG. 3) in relation to a location on biological tissue 108, the spotlight becomes weaker (for example, less bright and more diffused) on corresponding reconstructed 3D geometry 116. In some embodiments, when the distance between a particular electrode 120 and biological tissue 108 exceeds a proximity threshold value, no visual effect is produced for the particular electrode 120. In some embodiments, the user may select whether to always display a visual effect or to only display the visual effect for electrodes 120 that are closer than the proximity threshold value to the biological tissue 108. The proximity threshold value may be user selected or predetermined. In the example embodiment, the default proximity threshold value is four mm, but the user may select a different proximity threshold in a range from one mm to twelve mm. In other embodiments, the proximity threshold is fixed, i.e., not user variable, at four mm. In still other embodiments, the proximity threshold may be varied by the user within any other suitable range of distances.

As described above, visual effect 118 includes attributes that correspond to the actual proximity between catheter electrodes 120 and biological tissue 108. This further provides an even more accurate electrical mapping of catheter 106 and biological tissue 108. In the example embodiment, as explained above, one attribute includes a change in brightness of visual effect 118 as the proximity of electrode 120 and biological tissue 108 changes. Other attributes include, but are not limited to, a change in color intensity of visual effect 118, a decrease of the diffuseness of visual effect 118, and a change in transparency of reconstructed 3D geometry 116 surface relative to the proximity between electrode(s) 120 and biological tissue 108. For example, locations of the displayed reconstructed 3D geometry 116 may become less transparent as the proximity of electrode(s) 120 and biological tissue 108 decrease (i.e., as electrode(s) move closer to biological tissue 108).

Referring to FIG. 2, catheter image 202 is within a certain proximity to geometry 116. Catheter image 202 includes visual effects 118 in the form of spotlights 204, 206, 208, and 210 (as described above). The various sizes and color intensities illustrate different proximities between catheter 106 and biological tissue 108. Referring to FIG. 3, catheter 106 has moved to a second location within biological tissue 108, thus changing the proximity of electrodes 120 to biological tissue 108. As a result, visual effects 118 on catheter image 202 appear visually distinct from the appearance of visual effects 118 in the first location (FIG. 2). Specifically, spotlights 204, 206, and 210 appear less bright, more diffused, and illustrate a lower intensity of color. Spotlight 208 cannot be seen in the second location, indicating that the threshold proximity has been reached. The proximity threshold may be defined by the user or physician and programmed into processor 110.

Maps 200 and 300 show that the proximities between electrodes 120 and biological tissue 108 are smaller at the first location (FIG. 2) than at the second location (FIG. 3). By moving catheter 106 between positions in biological tissue 108, and viewing the changed attributes of visual effects 118, a physician is able to accurately guide catheter 106 through a blood vessel and into a biological region, such as the chamber of a heart.

With regard to both FIG. 2 and FIG. 3, it should be understood that spotlights 204, 206, 208, and 210 are all examples of one embodiment of visual effect 118.

Figure 4:
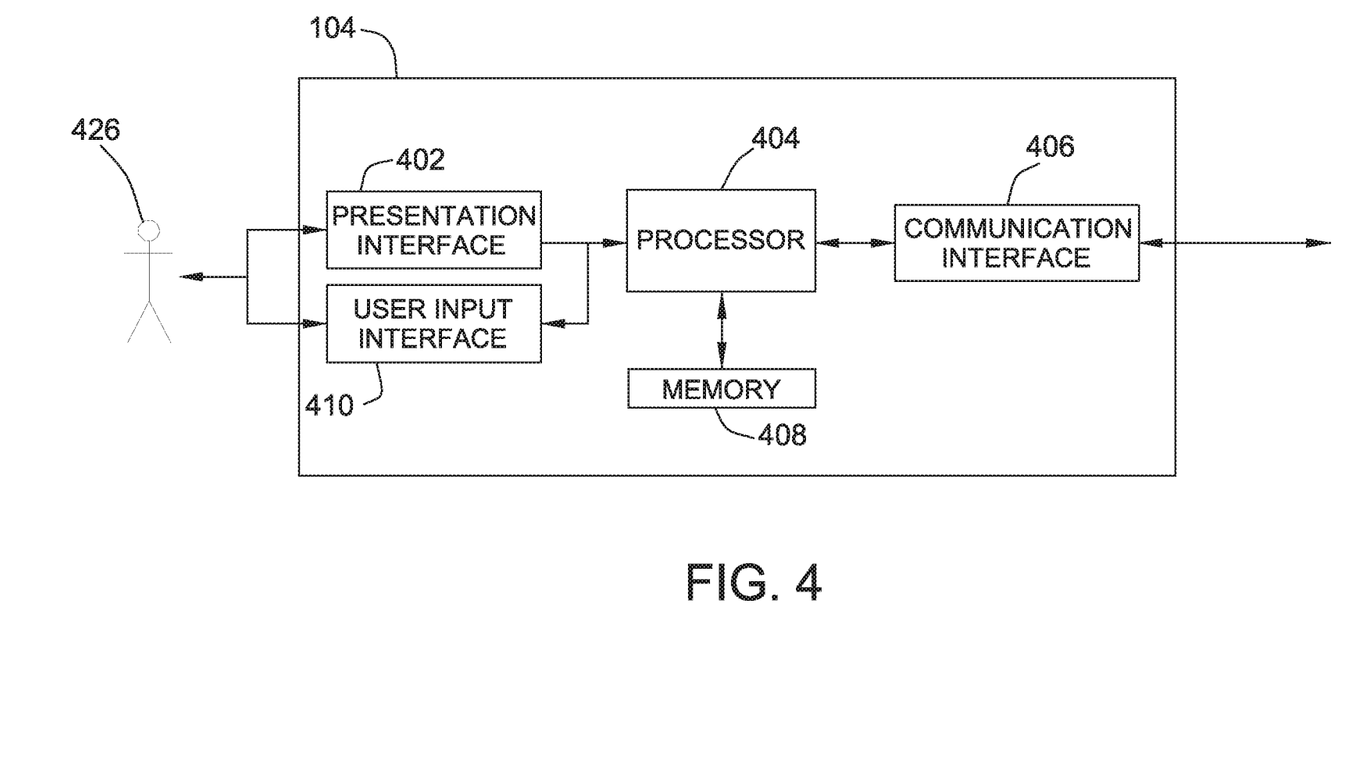
FIG. 4 illustrates an example configuration of a display device used in the system shown in FIG. 1.

FIG. 4 illustrates an example configuration of display device 104 used in system 100 shown in FIG. 1. Display device 104 may include, but is not limited to, a computer screen, and/or any device suitable for displaying a reconstructed digital 3D image. In the example embodiment, display device 104 includes a processor 404 for executing instructions. In some embodiments, executable instructions are stored in a memory area 408. Processor 404 may include one or more processing units, for example, a multi-core configuration. Memory area 408 is any device allowing information such as executable instructions and/or written works to be stored and retrieved. Memory area 408 may include one or more computer readable media.

Display device 104 also includes at least one media output component 410 for presenting information to user 426. Media output component 410 is any component capable of conveying information to user 426. In some embodiments, media output component 410 includes an output adapter such as a video adapter and/or an audio adapter. An output adapter is operatively coupled to processor 404 and operatively couplable to an output device such as a display device, a liquid crystal display (LCD), organic light emitting diode (OLED) display, or "electronic ink" display, or an audio output device, a speaker or headphones.

In some embodiments, display device 104 includes an input device 402 for receiving input from user 426. Input device 402 may include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output device of media output component 410 and input device 402. Display device 104 may also include a communication interface 406, which is capable of or configured to be communicatively coupled to a remote device such as the digital account. Communication interface 406 may include, for example, a wired or wireless network adapter or a wireless data transceiver for use with a mobile phone network, Global System for Mobile communications (GSM), 3G, or other mobile data network or Worldwide Interoperability for Microwave Access (WIMAX), or an 802.11 wireless network (WLAN).

Stored in memory area 408 are, for example, computer readable instructions for providing a user interface to user 426 via media output component 410 and, optionally, receiving and processing input from input device 402. A user interface may include, among other possibilities, a web browser and client application. Web browsers enable users, such as user 426, to display and interact with media and other information typically embedded on a web page or a website.

Figure 5:
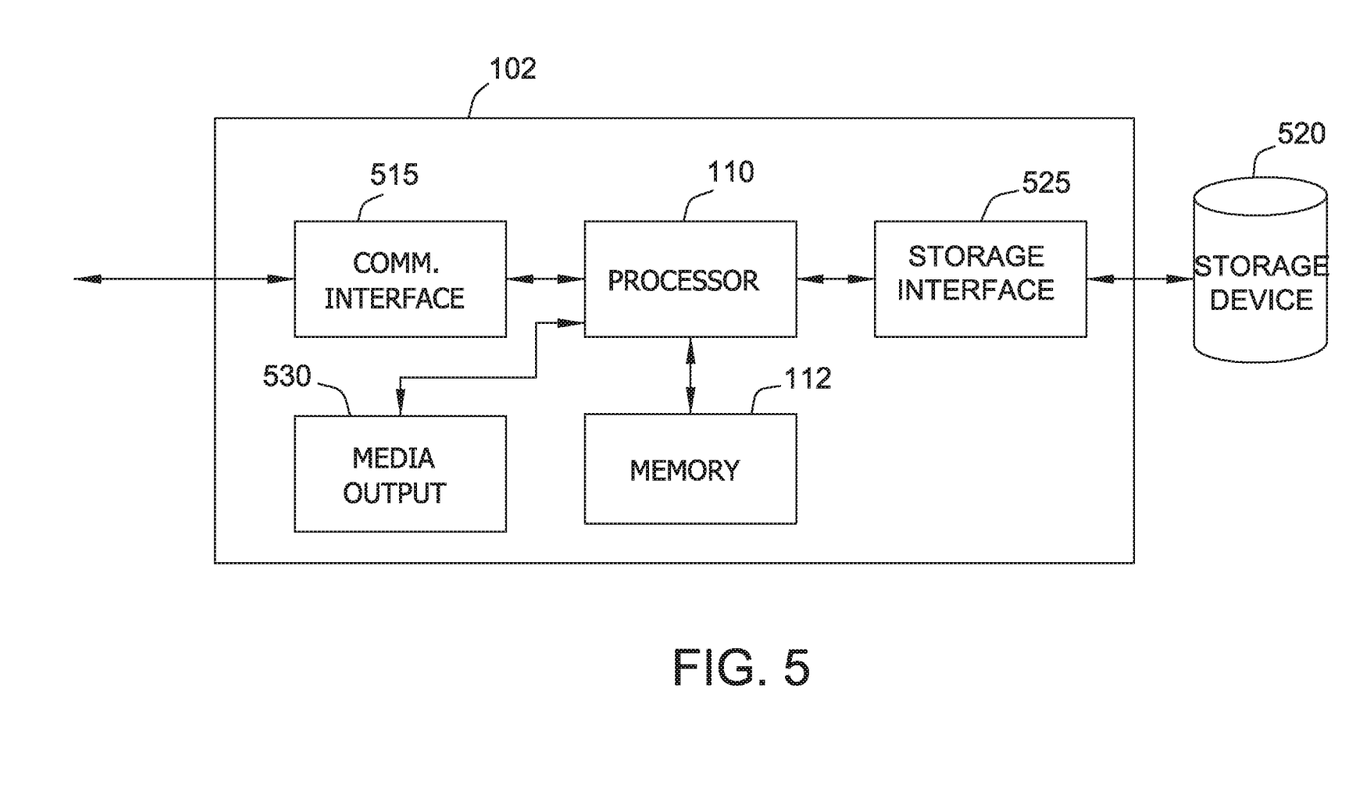
FIG. 5 illustrates an example configuration of a computing device used in the system as shown in FIG. 1.

FIG. 5 illustrates an example configuration of computing device 102 used in the system as shown in FIG. 1. Computing device 102 includes a processor 110 for executing instructions. Instructions may be stored in a memory area 112, for example. Processor 110 may include one or more processing units (e.g., in a multi-core configuration) for executing instructions. The instructions may be executed within a variety of different operating systems on the computing device 102, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or other suitable programming languages, etc.).

Processor 110 is operatively coupled to a communication interface 515 such that computing device 102 is capable of communicating with a remote device such as a user system, a catheter 106, a display device 104, or another computing device 102. Communication interface 515 may include, for example, a wired or wireless network adapter or a wireless data transceiver for use with a mobile phone network, Global System for Mobile communications (GSM), 3G, or other mobile data network or Worldwide Interoperability for Microwave Access (WIMAX).

Processor 110 may also be operatively coupled to a storage device 520. Storage device 520 is any computer-operated hardware suitable for storing and/or retrieving data. In some embodiments, storage device 520 is integrated in computing device 102. For example, computing device 102 may include one or more hard disk drives as storage device 520. In other embodiments, storage device 520 is external to computing device 102 and may be accessed by a plurality of computing devices 102. For example, storage device 520 may include multiple storage units such as hard disks or solid state disks in a redundant array of inexpensive disks (RAID) configuration. Storage device 520 may include a storage area network (SAN) and/or a network attached storage (NAS) system.

In some embodiments, processor 110 is operatively coupled to storage device 520 via a storage interface 525. Storage interface 525 is any component capable of providing processor 110 with access to storage device 520. Storage interface 525 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 110 with access to storage device 520.

Computing device 102 may also include at least one media output component 530 for presenting information, e.g., images, to user 426. Media output component 530 is any component capable of conveying information to user 426. In some embodiments, media output component 530 includes an output adapter such as a video adapter and/or an audio adapter. An output adapter is operatively coupled to processor 110 and operatively couplable to an output device such as a display device, a liquid crystal display (LCD), organic light emitting diode (OLED) display, or "electronic ink" display, or an audio output device, a speaker or headphones.

Memory 112 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

Stored in memory area 112 are, for example, computer readable instructions for providing a user interface to user 426 via media output component 530 and, optionally, receiving and processing input from input device 540, sensor interface 550, display device 104, and/or catheter 106. A user interface may include, among other possibilities, an image viewer and client application. Image viewers enable users, such as user 426, to display and interact with media and other information received from display device 104, and/or catheter 106. A client application allows user 426 to interact with display device 104, and/or catheter 106, e.g., requesting a frame to be captured.

Figure 6:
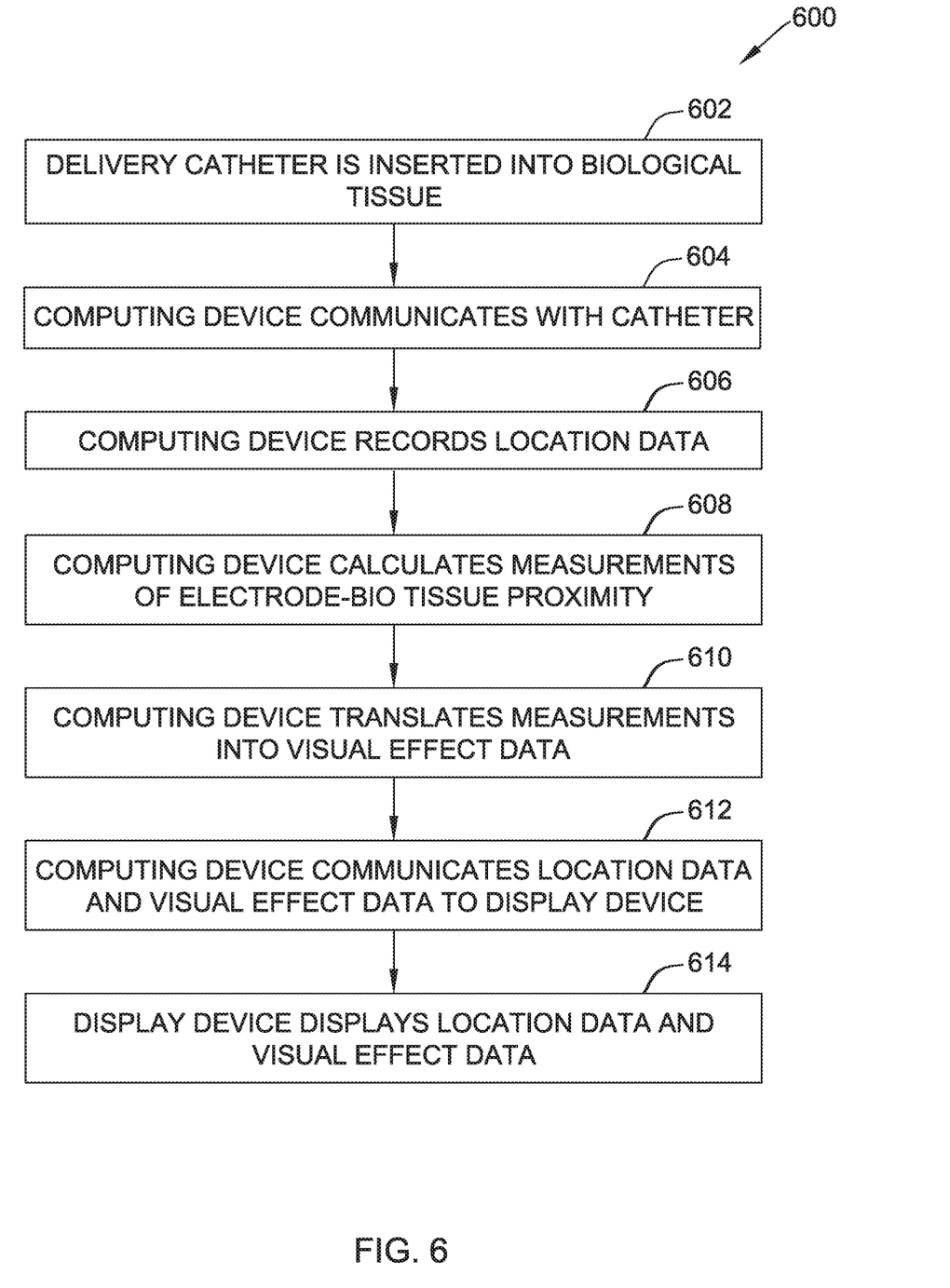
FIG. 6 is a flow diagram of a method for displaying electrodes and visual effects on an electrophysiological map during catheter navigation.

FIG. 6 is a flow diagram of a method 600 for using catheter navigation and mapping systems. FIG. 6 may represent, for example, an exemplary method for displaying electrodes and visual effects on an electrophysiology map during catheter navigation using the exemplary system described herein with respect to FIG. 1. A catheter, including a mounted tracking device and at least one electrode, is inserted 602 into the patient's heart at a location proximate a biological tissue for electrophysiological mapping. A computing device then communicates 604 with the catheter, either through a wired or wireless connection, and records 606 electrical location data retrieved from the catheter.

The computing device uses the recordings to calculate 608 measurements indicating the proximity of the electrodes within the catheter to the biological tissue. The computing device translates 610 the measurements into visual effect data. The computing device communicates 612 the electrical location data and the visual effect data to a display device. The display device displays 614 the location data and the visual effect data to the user on a display screen.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electrophysiology system to facilitate visualizing a proximity of at least one catheter electrode to a 3D geometry of a biological tissue, the system comprising:
   a computing device comprising:
      at least one processor in communication with a memory, wherein the processor is configured to:
         receive, from a catheter including the at least one catheter electrode, sensor data acquired using the catheter;
         calculate, from the received sensor data, at least one measurement;
         determine the proximity between the at least one catheter electrode and the biological tissue using the at least one measurement;
         generate an electrophysiology map illustrating a 3D geometry of the biological tissue alongside a visual effect and a catheter image, wherein the visual effect is a digital spotlight having a 2D shape that is projected onto a surface of the 3D geometry, wherein the digital spotlight indicates the proximity between the at least one catheter electrode and the biological tissue, and wherein the computing device determines a position of the digital spotlight on the 3D geometry based on a position of the at least one electrode relative to the biological tissue; and
         dynamically transform the projected digital spotlight to indicate various degrees of proximity between the at least one catheter electrode and the biological tissue as the at least one catheter electrode moves relative to the biological tissue; and
      a display device coupled to the computing device and configured to display the electrophysiology map.

2. The system according to claim 1, wherein the at least one measurement includes a shortest distance from a location of the at least one catheter electrode to a geometry surface of the biological tissue.

3. The system according to claim 1, wherein the at least one measurement includes a contact force, wherein the contact force is a positive value when the at least one catheter electrode is in contact with a biological surface.

4. The system according to claim 1, wherein the at least one measurement includes an electrode-tissue coupling index, and wherein the electrode-tissue coupling index is determined from a measured complex impedance when a voltage is applied to the at least one catheter electrode.

5. The system according to claim 1, wherein the at least one measurement includes a peak to peak voltage of an electrogram at the at least one catheter electrode.

6. The system according to claim 1, wherein the digital spotlight is a 2D circle shape.

7. The system according to claim 1, wherein the digital spotlight is centered at the position on the 3D geometry that has a shortest distance between the associated electrode and the surface of the 3D geometry.

8. The system according to claim 7, wherein the digital spotlight has a color, and wherein the intensity and brightness of the color increase when the proximity between the at least one catheter electrode and the 3D geometry decreases.

9. The system according to claim 7, wherein a diffuseness of the digital spotlight decreases when the proximity between the at least one catheter electrode and the 3D geometry decreases.

10. The system according to claim 7, wherein a transparency of the 3D geometry surface decreases when the proximity between the at least one catheter electrode and the 3D geometry decreases.

11. The system according to claim 10, wherein the digital spotlight disappears after a threshold proximity between the at least one catheter electrode and the 3D geometry is exceeded.

12. A method for displaying a distance between at least one catheter electrode and a 3D geometry of a biological tissue during 3D electrophysiology, the method comprising:
receiving, at a computing device including at least one processor in communication with a memory, from a catheter including the at least one catheter electrode, sensor data acquired using the catheter;
calculating, using the computing device, from the received sensor data, at least one measurement;
determining a proximity between the at least one catheter electrode and the biological tissue using the at least one measurement;
generating an electrophysiology map illustrating a 3D geometry of the biological tissue alongside a visual effect and a catheter image, wherein the visual effect is a digital spotlight having a 2D shape that is projected onto a surface of the 3D geometry, wherein the digital spotlight indicates the proximity between the at least one catheter electrode and the biological tissue, and wherein the computing device determines a position of the digital spotlight on the 3D geometry based on a position of the at least one electrode relative to the biological tissue;
dynamically transforming the projected digital spotlight to indicate various degrees of proximity between the at least one catheter electrode and the biological tissue as the at least one catheter electrode moves relative to the biological tissue; and
displaying, on a display device coupled to the computing device, the electrophysiology map.

13. The method according to claim 12, wherein the at least one measurement includes a shortest distance from a location of the at least one catheter electrode to a geometry surface of the biological tissue.

14. The method according to claim 12, wherein the at least one measurement includes a contact force, wherein the contact force is a positive value when the at least one catheter electrode is in contact with a biological surface.

15. The method according to claim 12, wherein the at least one measurement includes an electrode-tissue coupling index, and wherein the electrode-tissue coupling index is determined from a measured complex impedance when a voltage is applied to the at least one electrode.

16. The method according to claim 12, wherein the at least one measurement includes a peak to peak voltage of an electrogram at the at least one electrode.

17. The method according to claim 12, wherein the digital spotlight is a 2D circle shape.

18. The method according to claim 12, wherein the digital spotlight is centered at the position on the 3D geometry that has a shortest distance between the associated electrode and the surface of the 3D geometry.

19. The method according to claim 18, wherein the digital spotlight has a color, and wherein the intensity and brightness of the color increase when the proximity between the at least one electrode and the 3D geometry decreases.

20. The method according to claim 19, wherein a diffuseness of the digital spotlight decreases when the proximity between the at least one electrode and the 3D geometry decreases.

* * * * *